(12) United States Patent
Mehta et al.

(10) Patent No.: US 12,678,326 B2
(45) Date of Patent: Jul. 14, 2026

(54) SYSTEMS AND METHODS FOR CONTROLLING CONTINUOUS IRRIGATION IN SURGICAL SYSTEMS

(71) Applicant: Johnson & Johnson Surgical Vision, Inc., Irvine, CA (US)

(72) Inventors: Deep Mehta, Irvine, CA (US); Sandra Keh, Irvine, CA (US); Abraham Hajishah, Irvine, CA (US); Katrina Lieu, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 765 days.

(21) Appl. No.: 17/064,178

(22) Filed: Oct. 6, 2020

(65) Prior Publication Data

US 2021/0106734 A1     Apr. 15, 2021

Related U.S. Application Data

(60) Provisional application No. 62/913,669, filed on Oct. 10, 2019.

(51) Int. Cl.
   *A61F 9/007*        (2006.01)
   *A61M 1/00*         (2006.01)
      (Continued)

(52) U.S. Cl.
   CPC ...... *A61F 9/00736* (2013.01); *A61F 9/00745* (2013.01); *A61M 1/77* (2021.05);
      (Continued)

(58) Field of Classification Search
   CPC .... A61F 9/00736; A61F 9/00781; A61F 9/00; A61F 9/007; A61M 1/77; A61M 1/74;
      (Continued)

(56) References Cited

U.S. PATENT DOCUMENTS

| | | | |
|---|---|---|---|
| 2,094,830 A | 10/1937 | David |
| 2,842,331 A | 7/1958 | Anderson |

(Continued)

FOREIGN PATENT DOCUMENTS

| | | | |
|---|---|---|---|
| CN | 108323001 A | 7/2018 |
| CN | 116250982 A | 6/2023 |

(Continued)

OTHER PUBLICATIONS

Cionni R.J., "Evaluating Two Key Safety Advances In the Centurion Vision System", ALCON, Cataract and Refractive Surgery Today, Aug. 2019, 4 pages.

(Continued)

*Primary Examiner* — Scott J Medway

(57)                   ABSTRACT

The present invention comprises a fluid source connected to an irrigation feed line, an aspiration line providing at least a partial vacuum at a surgical site, at least one pressure sensor in communication with the aspiration line, and at least one valve in communication with the irrigation feed line, wherein the at least one valve restricts fluid flow in the irrigation feed line in accordance with at least one measurement of aspiration pressure differential and at least one predetermined system attribute, and wherein the aspiration pressure differential may equal a first measurement of aspiration pressure minus a second measurement of aspiration pressure over a predetermined time.

27 Claims, 8 Drawing Sheets

(51) Int. Cl.
    *A61M 3/02*       (2006.01)
    *A61M 39/22*     (2006.01)

(52) U.S. Cl.
    CPC ........ *A61M 3/0201* (2021.05); *A61M 3/0202*
        (2021.05); *A61M 3/025* (2013.01); *A61M*
        *39/22* (2013.01); *A61M 1/74* (2021.05); *A61M*
        *2205/3331* (2013.01); *A61M 2205/502*
        (2013.01); *A61M 2210/0612* (2013.01)

(58) Field of Classification Search
    CPC ........ A61M 2210/0612; A61M 3/0202; A61M
        3/0216; A61M 1/774; A61M 2205/50;
        A61M 2205/3344; A61M 3/0201
    See application file for complete search history.

(56)         References Cited

U.S. PATENT DOCUMENTS

| | | | |
|---|---|---|---|
| 3,393,566 A | 7/1968 | Malcolm et al. | |
| 3,575,301 A | 4/1971 | Panissidi | |
| 3,920,014 A | 11/1975 | Banko | |
| 3,994,421 A | 11/1976 | Hansen | |
| 4,274,411 A | 6/1981 | Dotson, Jr. | |
| 4,291,706 A | 9/1981 | Voges et al. | |
| 4,384,578 A | 5/1983 | Winkler | |
| 4,555,940 A | 12/1985 | Renger | |
| 4,653,719 A | 3/1987 | Cabrera et al. | |
| 4,680,445 A | 7/1987 | Ogawa | |
| 4,702,733 A | 10/1987 | Wright et al. | |
| 4,818,186 A | 4/1989 | Pastrone et al. | |
| 4,832,685 A | 5/1989 | Haines | |
| 4,902,034 A | 2/1990 | Maguran et al. | |
| 4,935,005 A | 6/1990 | Haines | |
| 4,954,960 A | 9/1990 | Lo et al. | |
| 5,032,111 A | 7/1991 | Morris et al. | |
| 5,047,009 A | 9/1991 | Morris et al. | |
| 5,106,367 A | 4/1992 | Ureche et al. | |
| 5,108,372 A | 4/1992 | Swenson | |
| 5,135,485 A | 8/1992 | Cohen et al. | |
| 5,167,620 A | 12/1992 | Ureche et al. | |
| 5,190,042 A | 3/1993 | Hock | |
| 5,242,404 A | 9/1993 | Conley et al. | |
| 5,328,456 A | 7/1994 | Horiguchi et al. | |
| 5,354,268 A | 10/1994 | Peterson et al. | |
| 5,405,269 A | 4/1995 | Stupecky | |
| 5,417,246 A | 5/1995 | Perkins et al. | |
| 5,429,601 A | 7/1995 | Conley et al. | |
| 5,476,448 A | 12/1995 | Urich | |
| 5,487,827 A | 1/1996 | Peterson et al. | |
| 5,569,188 A | 10/1996 | Mackool | |
| 5,591,127 A | 1/1997 | Barwick, Jr. et al. | |
| 5,616,120 A | 4/1997 | Andrew et al. | |
| 5,649,905 A | 7/1997 | Zanger et al. | |
| 5,693,013 A * | 12/1997 | Geuder | A61M 1/742 |
| | | | 604/35 |
| 5,695,473 A | 12/1997 | Olsen | |
| 5,697,898 A | 12/1997 | Devine | |
| 5,700,240 A | 12/1997 | Barwick, Jr. et al. | |
| 5,733,256 A | 3/1998 | Costin | |
| 5,766,146 A | 6/1998 | Barwick, Jr. | |
| 5,810,765 A * | 9/1998 | Oda | A61M 3/022 |
| | | | 604/35 |
| 5,827,223 A | 10/1998 | Butterfield | |
| 5,865,764 A | 2/1999 | Moorhead | |
| 5,885,243 A | 3/1999 | Capetan et al. | |
| 5,910,110 A | 6/1999 | Bastable | |
| 5,921,554 A | 7/1999 | Derian et al. | |
| 5,935,106 A | 8/1999 | Olsen | |
| 6,050,496 A | 4/2000 | Hefler | |
| 6,159,175 A | 12/2000 | Strukel et al. | |
| 6,167,588 B1 | 1/2001 | Dyson | |
| 6,170,383 B1 | 1/2001 | Mauritz | |
| 6,179,808 B1 | 1/2001 | Boukhny et al. | |
| 6,190,354 B1 | 2/2001 | Sell et al. | |

| | | | |
|---|---|---|---|
| 6,383,203 B1 | 5/2002 | Makihara | |
| 6,423,029 B1 | 7/2002 | Elsberry | |
| 6,491,661 B1 | 12/2002 | Boukhny et al. | |
| 6,533,747 B1 | 3/2003 | Polaschegg et al. | |
| 6,565,535 B2 | 5/2003 | Zaias et al. | |
| 6,579,255 B2 | 6/2003 | Kadziauskas et al. | |
| 6,599,271 B1 | 7/2003 | Easley | |
| 6,648,223 B2 | 11/2003 | Boukhny et al. | |
| 6,681,730 B1 | 1/2004 | Koneda et al. | |
| 6,740,058 B2 | 5/2004 | Lal et al. | |
| 6,780,166 B2 | 8/2004 | Kanda et al. | |
| 6,986,753 B2 | 1/2006 | Bui | |
| 7,083,591 B2 | 8/2006 | Cionni | |
| 7,146,864 B2 | 12/2006 | Sullivan et al. | |
| 7,297,137 B2 | 11/2007 | Gordon et al. | |
| 7,670,330 B2 | 3/2010 | Claus et al. | |
| 7,695,447 B2 | 4/2010 | Khashayar et al. | |
| 7,785,336 B2 | 8/2010 | Staggs | |
| 7,811,255 B2 * | 10/2010 | Boukhny | A61F 9/00745 |
| | | | 604/118 |
| 8,246,580 B2 | 8/2012 | Hopkins et al. | |
| 8,380,126 B1 | 2/2013 | Ma et al. | |
| 8,425,452 B2 | 4/2013 | Claus et al. | |
| 8,430,840 B2 | 4/2013 | Nazarifar et al. | |
| 8,430,841 B2 | 4/2013 | Claus et al. | |
| 8,444,592 B2 | 5/2013 | Williams et al. | |
| 8,479,585 B2 | 7/2013 | Shaw-klein | |
| 8,491,528 B2 | 7/2013 | Muri et al. | |
| 8,523,812 B2 | 9/2013 | Boukhny et al. | |
| 8,617,106 B2 | 12/2013 | Zacharias | |
| 8,652,086 B2 | 2/2014 | Gerg et al. | |
| 8,668,665 B2 | 3/2014 | Gerg et al. | |
| 8,715,220 B2 | 5/2014 | Gerg et al. | |
| 8,721,594 B2 | 5/2014 | Zacharias | |
| 9,198,798 B2 | 12/2015 | Claus et al. | |
| 9,482,563 B2 | 11/2016 | Calderin et al. | |
| 9,549,851 B2 * | 1/2017 | Chon | A61F 9/00736 |
| 9,610,193 B2 | 4/2017 | Velasco et al. | |
| 9,610,913 B2 | 4/2017 | Narita | |
| 9,782,232 B1 * | 10/2017 | Papac | A61F 9/00736 |
| 9,795,507 B2 | 10/2017 | Hajishah et al. | |
| 9,861,522 B2 | 1/2018 | Sorensen et al. | |
| 9,931,447 B2 | 4/2018 | Layser et al. | |
| 10,125,877 B2 | 11/2018 | Morgan et al. | |
| 10,182,940 B2 | 1/2019 | Chandrakant et al. | |
| 10,278,861 B2 | 5/2019 | Bourne | |
| 10,463,780 B2 | 11/2019 | Mallough et al. | |
| 10,470,926 B2 | 11/2019 | Zacharias | |
| 10,500,319 B2 | 12/2019 | Banko | |
| 10,518,005 B2 | 12/2019 | Carr et al. | |
| 10,702,415 B2 | 7/2020 | Charles | |
| 11,033,897 B2 | 6/2021 | Szita et al. | |
| 11,051,978 B2 * | 7/2021 | Heeren | A61M 3/0283 |
| 11,071,816 B2 | 7/2021 | Mehta et al. | |
| 11,185,623 B2 * | 11/2021 | Ovchinnikov | A61M 1/743 |
| 11,383,020 B2 | 7/2022 | Keh et al. | |
| 11,446,424 B2 | 9/2022 | Mehta et al. | |
| 11,602,586 B2 * | 3/2023 | Bourne | A61M 1/74 |
| 2001/0023331 A1 | 9/2001 | Kanda et al. | |
| 2002/0019607 A1 | 2/2002 | Bui | |
| 2002/0174910 A1 | 11/2002 | Willeke et al. | |
| 2002/0193817 A1 | 12/2002 | Lal et al. | |
| 2003/0006729 A1 | 1/2003 | Raymond | |
| 2003/0050613 A1 | 3/2003 | Hammerslag | |
| 2003/0050619 A1 | 3/2003 | Mooijman et al. | |
| 2003/0078487 A1 | 4/2003 | Jeffries et al. | |
| 2003/0105437 A1 | 6/2003 | Neubert | |
| 2004/0092885 A1 | 5/2004 | Duchon et al. | |
| 2004/0092921 A1 | 5/2004 | Kadziauskas et al. | |
| 2004/0101445 A1 | 5/2004 | Shvets et al. | |
| 2005/0054971 A1 * | 3/2005 | Steen | A61F 9/00745 |
| | | | 604/22 |
| 2005/0080375 A1 | 4/2005 | Kadziauskas et al. | |
| 2005/0096593 A1 | 5/2005 | Pope et al. | |
| 2005/0118048 A1 | 6/2005 | Traxinger | |
| 2005/0181018 A1 | 8/2005 | Peyman | |
| 2005/0209560 A1 | 9/2005 | Boukhny et al. | |
| 2005/0209621 A1 | 9/2005 | Gordon et al. | |
| 2005/0228423 A1 | 10/2005 | Khashayar et al. | |

(56) References Cited

U.S. PATENT DOCUMENTS

| | | |
|---|---|---|
| 2005/0234441 A1 | 10/2005 | Bisch et al. |
| 2005/0261628 A1 | 11/2005 | Boukhny et al. |
| 2005/0261715 A1 | 11/2005 | Boukhny et al. |
| 2005/0267504 A1 | 12/2005 | Boukhny et al. |
| 2006/0058811 A1 | 3/2006 | Kishimoto et al. |
| 2006/0064053 A1 | 3/2006 | Bollish et al. |
| 2006/0224107 A1 | 10/2006 | Claus et al. |
| 2006/0224143 A1 | 10/2006 | Claus et al. |
| 2006/0224163 A1 | 10/2006 | Sutton |
| 2006/0281986 A1 | 12/2006 | Orilla et al. |
| 2007/0005029 A1 | 1/2007 | Hopkins et al. |
| 2007/0227265 A1 | 10/2007 | Sugi et al. |
| 2007/0270744 A1 | 11/2007 | Dacquay et al. |
| 2008/0000485 A1 | 1/2008 | Williams et al. |
| 2008/0015406 A1 | 1/2008 | Dlugos et al. |
| 2008/0033349 A1 | 2/2008 | Suzuki |
| 2008/0053560 A1 | 3/2008 | Hartman et al. |
| 2008/0112828 A1 | 5/2008 | Muri et al. |
| 2008/0114289 A1 | 5/2008 | Muri et al. |
| 2008/0114290 A1 | 5/2008 | King et al. |
| 2008/0125698 A1 | 5/2008 | Gerg et al. |
| 2008/0154095 A1 | 6/2008 | Stubkjaer et al. |
| 2008/0177126 A1 | 7/2008 | Tate et al. |
| 2008/0319374 A1 | 12/2008 | Zacharias |
| 2008/0319451 A1 | 12/2008 | Zacharias |
| 2009/0013780 A1 | 1/2009 | Gao et al. |
| 2009/0048607 A1 | 2/2009 | Rockley |
| 2009/0158855 A1 | 6/2009 | Holden |
| 2009/0163863 A1 | 6/2009 | Lutwyche |
| 2009/0302671 A1 | 12/2009 | Brooks |
| 2010/0030134 A1 | 2/2010 | Fitzgerald et al. |
| 2010/0111735 A1 | 5/2010 | Tu |
| 2010/0121257 A1 | 5/2010 | King |
| 2010/0125246 A1 | 5/2010 | Kalpin |
| 2010/0130915 A1 | 5/2010 | Claus et al. |
| 2010/0145302 A1 | 6/2010 | Cull et al. |
| 2010/0174238 A1 | 7/2010 | Sher |
| 2010/0185150 A1 | 7/2010 | Zacharias |
| 2010/0249693 A1 | 9/2010 | Links |
| 2010/0280435 A1 | 11/2010 | Raney et al. |
| 2010/0292631 A1 | 11/2010 | Holden |
| 2010/0312170 A1 | 12/2010 | Maaskamp et al. |
| 2011/0027118 A1 | 2/2011 | Milovanovic |
| 2011/0087156 A1 | 4/2011 | Claus |
| 2011/0092891 A1 | 4/2011 | Gerg et al. |
| 2011/0092896 A1* | 4/2011 | Kuebler ................. A61M 1/74 604/30 |
| 2011/0112472 A1 | 5/2011 | Jacobson et al. |
| 2011/0152728 A1 | 6/2011 | Teodorescu |
| 2011/0257591 A1 | 10/2011 | Nelson Konen et al. |
| 2011/0284777 A1 | 11/2011 | Pitchford et al. |
| 2011/0295191 A1 | 12/2011 | Injev |
| 2011/0313343 A1 | 12/2011 | Milutinovic et al. |
| 2012/0004595 A1 | 1/2012 | Dubois et al. |
| 2012/0041362 A1 | 2/2012 | Gerg et al. |
| 2012/0265144 A1 | 10/2012 | Kalpin et al. |
| 2013/0060210 A1 | 3/2013 | Ross et al. |
| 2013/0060211 A1 | 3/2013 | Adams, Jr. |
| 2013/0062543 A1 | 3/2013 | Shiao et al. |
| 2013/0123680 A1 | 5/2013 | Ha et al. |
| 2013/0131578 A1 | 5/2013 | Stalmans et al. |
| 2013/0150782 A1 | 6/2013 | Sorensen et al. |
| 2013/0197471 A1 | 8/2013 | Williams et al. |
| 2013/0246079 A1 | 9/2013 | Hoffman et al. |
| 2014/0100518 A1 | 4/2014 | Baxter et al. |
| 2014/0107459 A1 | 4/2014 | Lind et al. |
| 2014/0114236 A1 | 4/2014 | Gordon et al. |
| 2014/0114237 A1 | 4/2014 | Gordon et al. |
| 2014/0163455 A1 | 6/2014 | Wilson et al. |
| 2014/0171869 A1 | 6/2014 | Zhang |
| 2014/0206940 A1 | 7/2014 | Hufford |
| 2014/0257172 A1 | 9/2014 | Yalamanchili |
| 2014/0282018 A1 | 9/2014 | Amble et al. |
| 2014/0323953 A1 | 10/2014 | Sorensen et al. |
| 2014/0364799 A1 | 12/2014 | Beauvais et al. |
| 2015/0057524 A1 | 2/2015 | Artsyukhovich et al. |
| 2015/0157501 A1 | 6/2015 | Bourne et al. |
| 2015/0359666 A1 | 12/2015 | Zacharias |
| 2016/0128869 A1 | 5/2016 | Zacharias |
| 2016/0175578 A1 | 6/2016 | Roholt |
| 2016/0220751 A1 | 8/2016 | Mallough et al. |
| 2016/0346123 A1 | 12/2016 | Koplin |
| 2016/0367735 A1 | 12/2016 | Eddo et al. |
| 2017/0022488 A1 | 1/2017 | Bermudez et al. |
| 2017/0224888 A1 | 8/2017 | Hickey et al. |
| 2017/0246419 A1 | 8/2017 | Callaghan et al. |
| 2017/0312431 A1 | 11/2017 | Johnson et al. |
| 2017/0326000 A1 | 11/2017 | Heeren et al. |
| 2017/0333253 A1* | 11/2017 | Heeren ............... A61F 9/00781 |
| 2017/0367885 A1 | 12/2017 | Bourne |
| 2017/0367887 A1 | 12/2017 | Muri et al. |
| 2018/0028359 A1 | 2/2018 | Gordon et al. |
| 2018/0049220 A1 | 2/2018 | Patil et al. |
| 2018/0049920 A1 | 2/2018 | Charles |
| 2018/0078415 A1 | 3/2018 | Citterio et al. |
| 2018/0092774 A1 | 4/2018 | Mehta et al. |
| 2018/0279876 A1 | 10/2018 | Paschalis |
| 2018/0296738 A1 | 10/2018 | King et al. |
| 2018/0304012 A1 | 10/2018 | Jansen |
| 2018/0318131 A1* | 11/2018 | Boukhny ............ A61M 3/0233 |
| 2018/0338861 A1 | 11/2018 | Hallen |
| 2019/0099526 A1 | 4/2019 | Hajishah et al. |
| 2019/0099529 A1 | 4/2019 | Mehta et al. |
| 2019/0099546 A1 | 4/2019 | Keh et al. |
| 2019/0099547 A1 | 4/2019 | Mehta et al. |
| 2019/0099548 A1 | 4/2019 | Mehta et al. |
| 2019/0133822 A1 | 5/2019 | Banko |
| 2019/0143008 A1 | 5/2019 | Brundage et al. |
| 2019/0176557 A1 | 6/2019 | Marking et al. |
| 2019/0200885 A1 | 7/2019 | Jacobsen |
| 2019/0262175 A1 | 8/2019 | Kerkhoff et al. |
| 2019/0282401 A1 | 9/2019 | Sorensen et al. |
| 2019/0365567 A1 | 12/2019 | Balkenbush et al. |
| 2020/0030147 A1 | 1/2020 | Koplin |
| 2020/0107958 A1 | 4/2020 | Wong et al. |
| 2020/0337900 A1 | 10/2020 | Nazarifar et al. |
| 2020/0360594 A1 | 11/2020 | Dam-huisman |
| 2021/0153741 A1 | 5/2021 | Berdahl et al. |
| 2021/0353145 A1 | 11/2021 | Kamthan et al. |
| 2021/0386927 A1 | 12/2021 | Mehta et al. |
| 2021/0386928 A1 | 12/2021 | Mehta et al. |
| 2022/0133537 A1 | 5/2022 | Govari et al. |
| 2022/0192876 A1* | 6/2022 | Algawi ............... A61M 3/0202 |
| 2022/0192877 A1 | 6/2022 | Algawi et al. |
| 2022/0193322 A1 | 6/2022 | Govari et al. |
| 2023/0190525 A1 | 6/2023 | Yan et al. |
| 2023/0390478 A1 | 12/2023 | Fung et al. |
| 2024/0108503 A1 | 4/2024 | Gliner et al. |
| 2024/0115421 A1 | 4/2024 | Govari et al. |
| 2024/0207092 A1 | 6/2024 | Govari |

FOREIGN PATENT DOCUMENTS

| | | |
|---|---|---|
| DE | 19753636 A1 | 9/1999 |
| DE | 20318275 U1 | 2/2004 |
| EP | 0997363 A2 | 5/2000 |
| EP | 1382291 A2 | 1/2004 |
| EP | 1471342 A2 | 10/2004 |
| EP | 1900347 A1 | 3/2008 |
| EP | 1471342 B1 | 8/2009 |
| EP | 2320842 A2 | 5/2011 |
| EP | 2379126 A2 | 10/2011 |
| EP | 2164435 B1 | 8/2012 |
| EP | 2919850 B1 | 10/2018 |
| JP | 62500640 T | 3/1987 |
| JP | 2001161740 A2 | 6/2001 |
| JP | 2003225247 A | 8/2003 |
| RU | 2720821 C1 | 5/2020 |
| WO | 8906522 A2 | 7/1989 |
| WO | 9945868 A1 | 9/1999 |
| WO | 0194893 A1 | 12/2001 |
| WO | 03047653 A1 | 6/2003 |
| WO | 04108189 A2 | 12/2004 |
| WO | 04110524 A2 | 12/2004 |

(56) References Cited

FOREIGN PATENT DOCUMENTS

| WO | 05037156 | A1 | | 4/2005 | | |
|----|----------|----|----|--------|----|----|
| WO | 2007143797 | A1 | | 12/2007 | | |
| WO | 2008030872 | A1 | | 3/2008 | | |
| WO | 2008157674 | A1 | | 12/2008 | | |
| WO | 2009076717 | A1 | | 6/2009 | | |
| WO | 2009076717 | A9 | | 8/2009 | | |
| WO | 2010124755 | A1 | | 11/2010 | | |
| WO | 2011045033 | A1 | | 4/2011 | | |
| WO | 2011105909 | A1 | | 9/2011 | | |
| WO | 2014151209 | A1 | | 9/2014 | | |
| WO | 2016122790 | A1 | | 8/2016 | | |
| WO | 2016150754 | A1 | | 9/2016 | | |
| WO | WO-2016148754 | A1 | * | 9/2016 | ............. | A61F 9/008 |
| WO | 2016191665 | A1 | | 12/2016 | | |
| WO | WO-2017044138 | A1 | * | 3/2017 | ....... | A61F 13/00068 |
| WO | 2018033877 | A1 | | 2/2018 | | |
| WO | 2018064625 | A1 | | 4/2018 | | |
| WO | 2019068151 | A1 | | 4/2019 | | |
| WO | 2019115584 | A1 | | 6/2019 | | |
| WO | 2021083938 | A1 | | 5/2021 | | |

OTHER PUBLICATIONS

Gopesh T., et al., "Rapid and Accurate Pressure Sensing Device for Direct Measurement of Intraocular Pressure", Translational Vision Science and Technology (TVST), Feb. 2020, vol. 9 (3), Article 28, pp. 1-9.

Bello S., et al., Development of a Smart Pump for Monitoring and Controlling Intraocular Pressure, Annals of Biomedical Engineering, Apr. 2017, vol. 45(4), pp. 990-1002.

Miller et al., "Millennial Eye", Supplement to Contract & Refractive Surgery Today, pp. 1-16, Sep./Oct. 2019.

Thomas_et_al, "Phaco Machine basics", Pearls in Ophthalmology, 5 pages, Jul. 17, 2010.

Yao et al., "A Flexible and Highly Sensitive Piezoresistive Pressure Sensor Based on Micropatterned Films Coated with Carbon Nanotubes", Journal of Nanomaterials, pp. 1-6, 2016.

* cited by examiner

SYSTEMS AND METHODS FOR CONTROLLING CONTINUOUS IRRIGATION IN SURGICAL SYSTEMS

CROSS-REFERENCE TO RELATED APPLICATIONS

This application claims the benefit under 35 U.S.C. § 119(e) of U.S. Provisional Patent Application No. 62/913,669 filed Oct. 10, 2019, which is incorporated herein by reference in its entirety.

FIELD OF THE INVENTION

The present invention relates to phacoemulsification fluidics system control, and, more particularly to systems and methods for controlling continuous irrigation in surgical systems.

BACKGROUND

Cataracts affect more than 22 million Americans age 40 and older. And as the U.S. population ages, more than 30 million Americans are expected to have cataracts by the year 2020. Cataract surgery entails the removal of a lens of an eye that has developed clouding of the eye's natural lens, or opacification. As a result of opacification, light is unable to travel to the retina, thereby causing vision loss. Once vision becomes impaired, cataract surgery is a viable option with a high level of success. During cataract surgery, a surgeon replaces the clouded lens with an intraocular lens (IOL).

Certain surgical procedures, such as phacoemulsification surgery, have been successfully employed in the treatment of certain ocular problems, such as cataracts. Phacoemulsification surgery utilizes a small corneal incision to insert the tip of at least one phacoemulsification handheld surgical implement, or handpiece, through the corneal incision. The handpiece includes a needle which is ultrasonically driven once placed within the incision to emulsify the eye lens, or to break the cataract into small pieces. The broken cataract pieces or emulsified eye lens may subsequently be removed using the same handpiece, or another handpiece, in a controlled manner. The surgeon may then insert an IOL into the eye through the incision. The incision is allowed to heal, and the result for the patient is typically significantly improved eyesight.

During the phacoemulsification process for cataract removal, a single plastic cassette (which may be disposable or reusable) is generally used to collect effluent material. This single cassette requires a prime on every insertion. The cost per case is a very sensitive factor for surgeons, which includes balanced salt solution ("BSS") usage and cassette cost. Currently a significant portion of BSS is used during prime to fill the line from the BSS bottle or bag to the pack. Time and coordination is also required for a non-sterile nurse to spike and hang the BSS bottle after the sterile nurse has inserted the cassette. This can slow down the setup procedure as the sterile nurse may be waiting for this to occur to start prime. The irrigation side of the cassette has maintained sterility, but since it is physically part of the cassette, it is typically disposed of at the end of a case, in some cases along with the BSS bottle.

Current phacoemulsification platforms provide two methods to activate irrigation during surgery: a graphical user interface (GUI) button and a foot pedal control to toggle irrigation. Many systems provide a continuous irrigation button on the graphical user interface which toggles the irrigation on and off. When continuous irrigation is on, the system actuates the irrigation valve to let the irrigation fluid from the source to reach the distal end of the surgical hand piece via a sleeve. A surgeon can also choose to activate irrigation with foot pedal control. In this case, a foot pedal treadle travel is divided into three segments: irrigation, irrigation/aspiration and irrigation/aspiration/ultrasound power. When a surgeon pushes the foot pedal treadle to the first position of the travel, the system actuates the irrigation valve to an on position. On the other hand, when the surgeon moves the treadle back up to the initial position (foot pedal position zero (FP0)) or foot pedal idle position, the system actuates the irrigation valve to the off position. In addition, a foot pedal switch can be programmed to turn on or turn off continuous irrigation or use the foot pedal tapping feature to accomplish the same result. Having a foot pedal control often helps the surgeon in turning the irrigation off when traversing between phacoemulsification (phaco), irrigation and aspiration (IA) and vitrectomy (Vit) modes of the surgery, but does so at the physical control of the operator and may be latent in the desired or optimal time for such functionality to occur. Similarly, use of a continuous irrigation button on a GUI does not allow a surgeon to control the irrigation when traversing between surgical modes except pressing the GUI button prior to switching the surgical mode. Thus, the need exists for the automated control of continuous irrigation in a surgical system.

BRIEF SUMMARY OF THE INVENTION

The present invention provides for a surgical system, comprising a fluid source connected to an irrigation feed line, an aspiration line providing at least a partial vacuum at a surgical site, at least one pressure sensor in communication with the aspiration line, and at least one valve in communication with the irrigation feed line, wherein the at least one valve restricts fluid flow in the irrigation feed line in accordance with at least one measurement of aspiration pressure differential and at least one predetermined system attribute, and wherein the aspiration pressure differential is equal to a first measurement of aspiration pressure minus a second measurement of aspiration pressure over a predetermined time.

BRIEF DESCRIPTION OF THE DRAWINGS

This disclosure is illustrated by way of example and not by way of limitation in the accompanying figure(s). The figure(s) may, alone or in combination, illustrate one or more embodiments of the disclosure. Elements illustrated in the figure(s) are not necessarily drawn to scale. Reference labels may be repeated among the figures to indicate corresponding or analogous elements.

The detailed description makes reference to the accompanying figures in which.

DETAILED DESCRIPTION

Figure 1A:
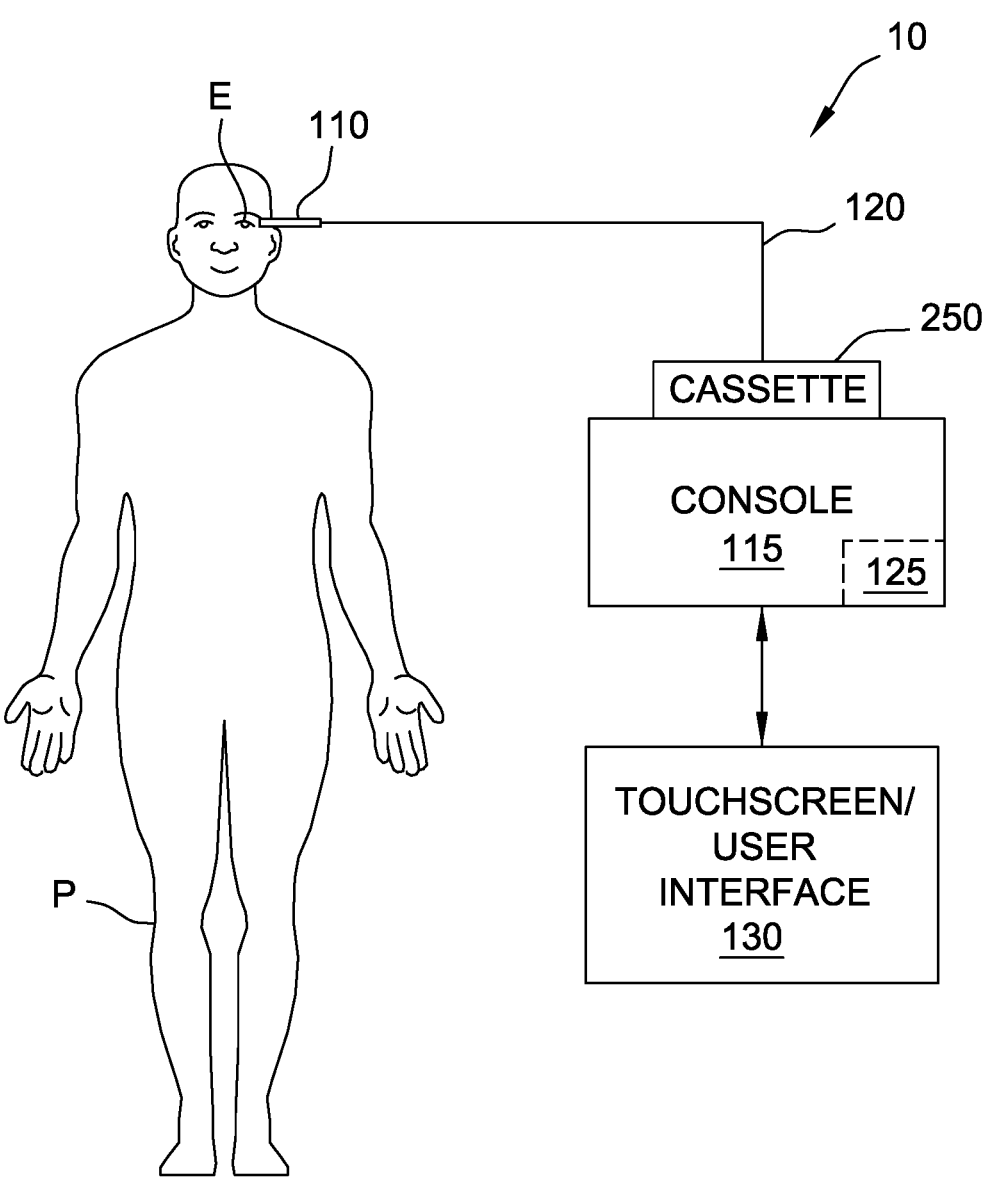
FIG. 1A is a schematic illustrating an eye treatment system in which a cassette is coupled to an eye treatment probe with an eye treatment console under one embodiment.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

The disclosed allows for the irrigation functionality of a phacoemulsification system to be decoupled from the aspiration, thus allowing for extended use of an irrigation cassette across multiple patients, minimizing cost per case, as well as setup time for the surgical center.

Phacoemulsification platforms may provide two main methods to activate irrigation during surgery: a graphical user interface (GUI) button and/or a foot pedal control to toggle irrigation. Phacoemulsification systems which provide a continuous irrigation function usually do so through a button actuation on a GUI which may toggle the irrigation on and off. When continuous irrigation is on, the system actuates the irrigation valve to let the irrigation fluid from the source reach the distal end of the surgical hand piece via a sleeve. When continuous irrigation is turned off, the system actuates the irrigation valve to an off position to stop the irrigation fluid from reaching the distal end of the hand piece.

A surgeon may also choose to activate the irrigation with foot pedal control. In such a case, a foot pedal treadle travel may be divided into three segments: irrigation, irrigation/ aspiration and irrigation/aspiration/ultrasound power. For example, when a surgeon pushes the foot pedal treadle to a first position of travel, the system may actuate the irrigation valve to an on position. Similarly, when a surgeon moves the treadle back up to an initial position or foot pedal idle position, for example, the system may actuate the irrigation valve to an off position. Having a foot pedal control often helps the surgeon in turning the irrigation off when traversing between phaco, IA or vitrectomy modes of the surgery whereas with continuous irrigation button on the GUI, the surgeon is not able to control the irrigation when traversing between surgical modes except by (1) pressing the GUI button prior to switching the surgical mode; (2) programming a switch or button on a foot pedal to turn on or turn off continuous irrigation; or (3) use a foot pedal tapping feature to accomplish the same result.

Referring now to FIG. 1A, a system 10 for treating an eye E of a patient P generally includes an eye treatment probe handpiece 110 coupled with a console 115 by a cassette 250. Handpiece 110 generally includes a handle for manually manipulating and supporting an insertable probe tip. The probe tip has a distal end which is insertable into the eye, with one or more lumens in the probe tip allowing irrigation fluid to flow from console 115 and/or cassette 250 into the eye. Aspiration fluid may also be withdrawn through a lumen of the probe tip, with console 115 and cassette 250 generally including a vacuum aspiration source, a positive displacement aspiration pump, or both to help withdraw and control a flow of surgical fluids into and out of eye E. As the surgical fluids may include biological materials that should not be transferred between patients, cassette 250 will often comprise a sterilizable (or alternatively, disposable) structure, with the surgical fluids being transmitted through flexible conduits 120 of cassette 250 that avoid direct contact in between those fluids and the components of console 115.

When a distal end of the probe tip of handpiece 110 is inserted into an eye E, for example, for removal of a lens of a patient P with cataracts, an electrical conductor and/or pneumatic line (not shown) may supply energy from console 115 to an ultrasound transmitter of handpiece 110, a cutter mechanism, or the like. Alternatively, handpiece 110 may be configured as an IA and/or vitrectomy handpiece. Also, the ultrasonic transmitter may be replaced by other means for emulsifying a lens, such as a high energy laser beam. The ultrasound energy from handpiece 110 helps to fragment the tissue of the lens, which can then be drawn into a port of the tip by aspiration flow. To balance the volume of material removed by the aspiration flow, an irrigation flow through handpiece 110 (or a separate probe structure) may also be provided, with both the aspiration and irrigation flows being controlled by console 115.

To avoid cross-contamination between patients without incurring excessive expenditures for each procedure, cassette 250 and its flexible conduits 120 may be disposable. However, the flexible conduit or tubing may be disposable, with the cassette body and/or other structures of the cassette being sterilizable. Cassette 250 may be configured to interface with reusable components of console 115, including, but not limited to, peristaltic pump rollers, a Venturi or other vacuum source, a controller 125, and/or the like.

Console 115 may include controller 125, which may include an embedded microcontroller and/or many of the components common to a personal computer, such as a processor, data bus, a memory, input and/or output devices (including a user interface 130 (e.g. touch screen, graphical user interface (GUI), etc.), and the like. Controller 125 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 125 may have (or be coupled with) a recording media reader, or the code may be transmitted to controller 125 by a network connection such as an internet, an intranet, an ethernet, a wireless network, or the like. Along with programming code, controller 125 may include stored data for implementing the methods described herein and may generate and/or store data that records parameters corresponding to the treatment of one or more patients.

Figure 1B:
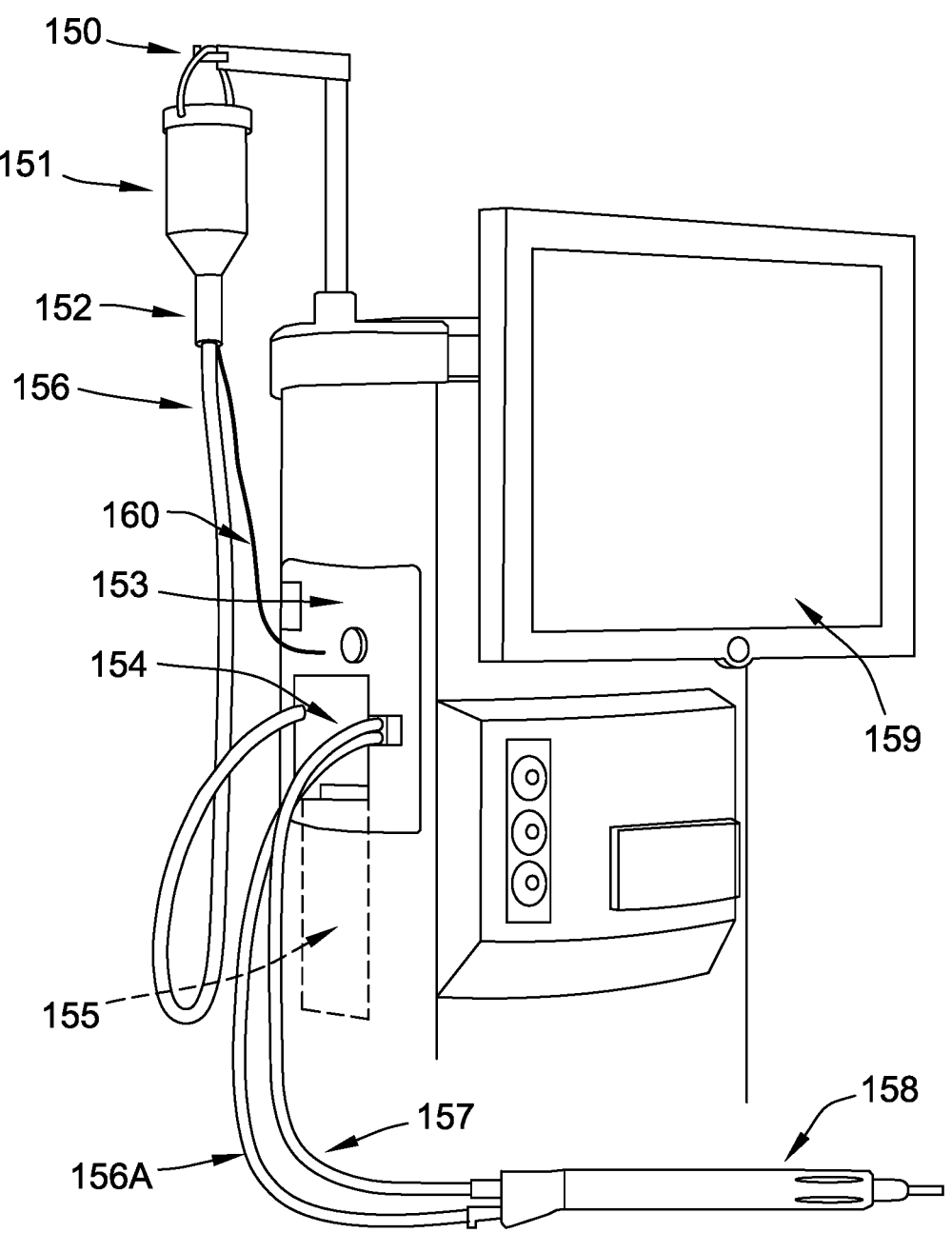
FIG. 1B is a schematic illustrating a surgical eye treatment console under another exemplary embodiment.

Referring now to FIG. 1B, a simplified surgical console is illustrated, where a fluid path may be demonstrated under an exemplary embodiment. In this example, an irrigation source 151 may be configured as a bottle or bag hanging from an IV pole hanger 150. It is understood by those skilled in the art that, while an integrated IV pole is illustrated, other configurations, utilizing standalone/static IV poles, or other suitable configurations, are contemplated by the present disclosure. In addition, the irrigation source may be located within the system console.

An exemplary irrigation path for fluid may be realized via tubing cassette 154 having cassette tubing interface 153, which receives fluid from irrigation source 151 via drip chamber 152. Irrigation line 156A and aspiration line 157 are coupled to handpiece 158. Irrigation fluid may flow from drip chamber 152 through the irrigation tubing 156 into tubing cassette 154. Irrigation fluid may then flow from the tubing cassette 154 through handpiece irrigation line 156A which may be coupled to an irrigation port on handpiece 158. Aspirated fluid may flow from handpiece aspiration line 157 back to tubing cassette 154 and into a waste collection bag 155. A touch screen display 159 may be provided to display system operation conditions and parameters, and may include a user interface (e.g., touch screen, keyboard, track ball, mouse, etc.—see controller 125 of FIG. 1A) for entering data and/or instructions to the system of FIG. 1B.

The present invention provides a system and method for turning off continuous irrigation within the surgical system when a surgeon removes the hand piece out of the eye (i.e. anterior chamber) and, for example, turns the continuous irrigation back on when hand piece is reinserted to proceed with the next step of the surgery. Typically, once substantially all the cataract particles are emulsified and evacuated out of the chamber using a phaco hand piece, the surgeon may remove the hand piece out of the chamber, disconnects the irrigation and aspiration luers from the phaco hand piece, and connects them to the IA hand piece. The IA hand piece may then be inserted into the chamber using the same incision.

Figure 2:
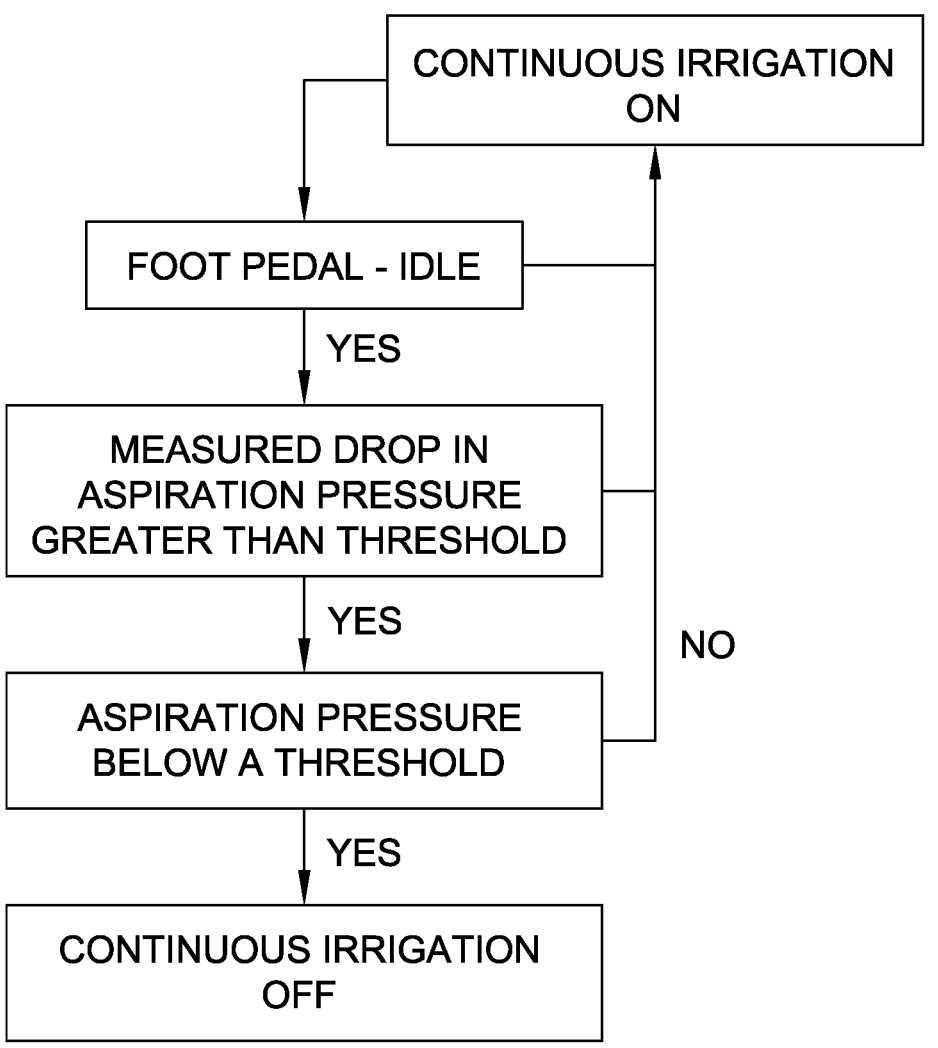
FIG. 2 is a flow diagram illustrating an exemplary embodiment of the disclosed invention.

When performing vitrectomy, the aspiration luer may be connected to the vitrectomy hand piece and the irrigation luer may be either connected to the vitrectomy hand piece or to a trocar instrument with a separate incision. The present invention may turn the continuous irrigation off when certain trigger events are detected. As illustrated in FIG. 2, such trigger events may include, but are not limited to the following conditions:

1. Continuous irrigation is on and the feature is activated by pressing the foot pedal down out of zone zero at least once AND
2. Foot pedal treadle is at Idle (FP 0) position AND
3. Aspiration pressure is decreasing at a rate greater than a certain specified value or dropped to a specified limit AND
4. Aspiration pressure is at certain specified value below a governing bottle/bag height pressure.

In an embodiment of the present invention, the system may turn the continuous irrigation off when one or more trigger events are detected during, for example, phaco, IA, or Vit sub-modes. By way of non-limiting example, the present invention may turn on continuous irrigation if one or more of the following trigger events are detected in the phaco/IA/Vit sub-mode:

1. Continuous irrigation was turned off manually or automatically AND
2. Foot pedal treadle is at irrigation (foot pedal 1 (FP1)) or irrigation/aspiration (FP2) or irrigation/aspiration/ ultrasound power (FP3) position.

In an alternative embodiment, a user of the present invention, such as a surgeon, for example, may turn the continuous irrigation on manually by pressing a GUI presented switch prior to reentering the chamber. The proposed auto turn-off feature may be enabled once the continuous irrigation button is pressed or selected on the GUI or a switch/button on the foot pedal is activated. The auto turn off feature may be disabled when the continuous irrigation button is deselected on the GUI or the switch/button on the foot pedal is activated.

In an embodiment, continuous irrigation may be turned off when a user changes from one sub-mode to another, e.g. phaco to IA.

Figure 3A:
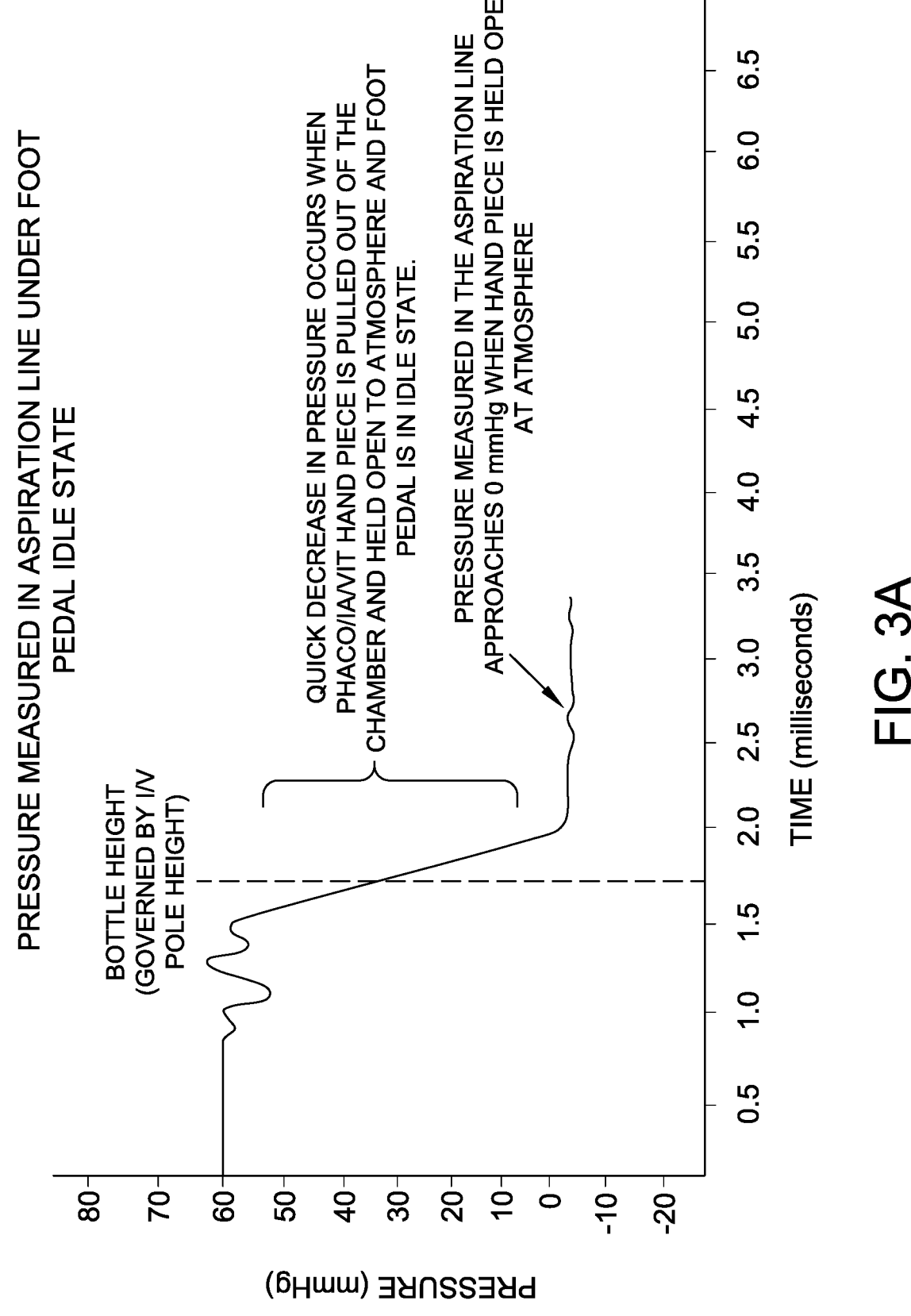
FIGS. 3A and 3B illustrate system conditions accordance with another exemplary embodiment of the disclosed invention.
Figure 3B:
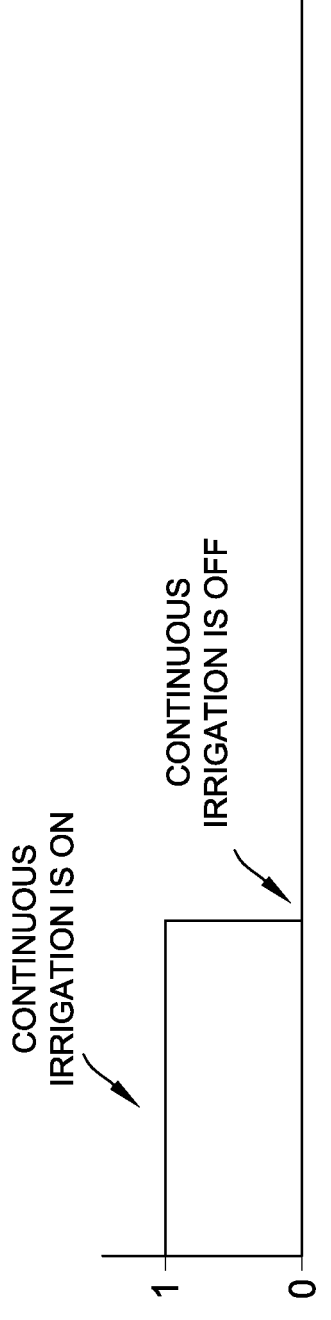

As illustrated in FIG. 3A, aspiration pressure, as represented on the x-axis, versus time changes when the Phaco/ IA/Vit hand piece is pulled out of the eye chamber and held open to atmosphere. For example, aspiration pressure may be set to about 60 mmHg as at least partially influenced by gravity fed irrigation delivered to the surgical site. The removal of the surgical handpiece from the surgical site opens the handpiece to atmospheric pressure and the measured aspiration pressure may begin to rapidly drop towards 0 mmHg. The auto-turn off feature of the present invention may use the aspiration line pressure measurements to determine if the hand piece is out of the surgical site and is under foot pedal idle state, which may then cause the continuous irrigation to be turned off. As illustrated in FIG. 3B, with its x-axis aligned with the FIG. 3A, the drop in aspiration pressure may trigger a continuous irrigation off condition. In an embodiment of the present invention, a drop in pressure of more than 20 mmHg, for example, may be at least a partial trigger. Such a drop may, for example occur in less than 2.0 milliseconds.

The triggers of various drops in pressure versus time may be associated with various predetermined thresholds and may encompass a wide range. For example, a predetermined drop in pressure may be in the range of about 15 mmHg to about 40 mmHg and maybe preferably about 30 mmHg. The time over which a drop in pressure occurs may be from about 2.5 milliseconds to about 0.5 milliseconds. The shorter the time chosen may increase responsiveness of the system. Additionally, pairing these thresholds with other demonstrative features occurring within the use of the system, such as, for example, foot pedal position, aids in the eliminated of switching off the continuous irrigation in a situation where it is still desired by the user of the system.

In alternate embodiment, a GUI feature may be provided to select/deselect the continuous irrigation auto-on and auto-off feature in addition to continuous irrigation toggle button. In an embodiment of the present invention, the continuous irrigation may be put into the off condition when the following trigger events are detected in phaco/IA/Vit sub-mode:

1. Continuous irrigation is on and the feature is activated by pressing the foot pedal down out of the zone zero at least once AND
2. Foot pedal treadle is at Idle (FP0) position AND
3. Aspiration pressure is at certain specified value below the governing bottle/bag height pressure AND
4. A change in sub-mode has occurred. (for example, Phaco to IA, IA to Vit).

In an embodiment, the proposed invention may turn the continuous irrigation off when following trigger events are detected in Phaco/IA/Vit sub-mode:

1. Continuous irrigation is on and the auto on is activated by pressing the foot pedal down out of the zone zero AND
2. Foot pedal treadle is at Idle (FP0) position AND
3. Aspiration pressure is decreasing at rate greater than certain specified value AND
4. Aspiration pressure is at certain specified value below the governing bottle/bag height pressure AND
5. A change in sub-mode has occurred.

In an embodiment of the present invention, the system may comprise a fluid source connected to an irrigation feed line, an aspiration line providing at least a partial vacuum at a surgical site, at least one pressure sensor in communication with the aspiration line, and at least one valve in communication with the irrigation feed line, wherein the at least one valve restricts fluid flow in the irrigation feed line in accordance with at least one measurement of aspiration pressure differential and at least one predetermined system attribute, and wherein the aspiration pressure differential is equal to a first measurement of aspiration pressure minus a second measurement of aspiration pressure over a predetermined time. The system may provide for a gravity fed fluid source and a pressurized fluid source. The aspiration pressure differential may be equal to about 20 mmHg and may be between about 20 mmHg and 40 mmHg. The predetermined time used by the system may range from about 2.5 milliseconds to about 0.5 milliseconds. Similarly, the system may make a first measurement upon a change in measured aspiration pressure of greater than about 5%.

In an embodiment of the present invention, a method for controlling fluid flow in a phacoemulsification surgical system is provided and comprises measuring a change in aspiration pressure, and restricting fluid flow in an irrigation feed line by at least one valve in accordance with the change in aspiration pressure and at least one system attribute, wherein the change in aspiration pressure may be equal to a first measurement of aspiration pressure minus a second measurement of aspiration pressure over a period of time. The at least one predetermined system attribute may be selected from the group consisting of foot pedal position, a minimum aspiration pressure; and a change in operation mode. The change in aspiration pressure may be equal to about 20 mmHg and may range between about 20 mmHg and 40 mmHg. The measuring may occur from about every 2.5 milliseconds to about every 0.5 milliseconds.

Figure 4:
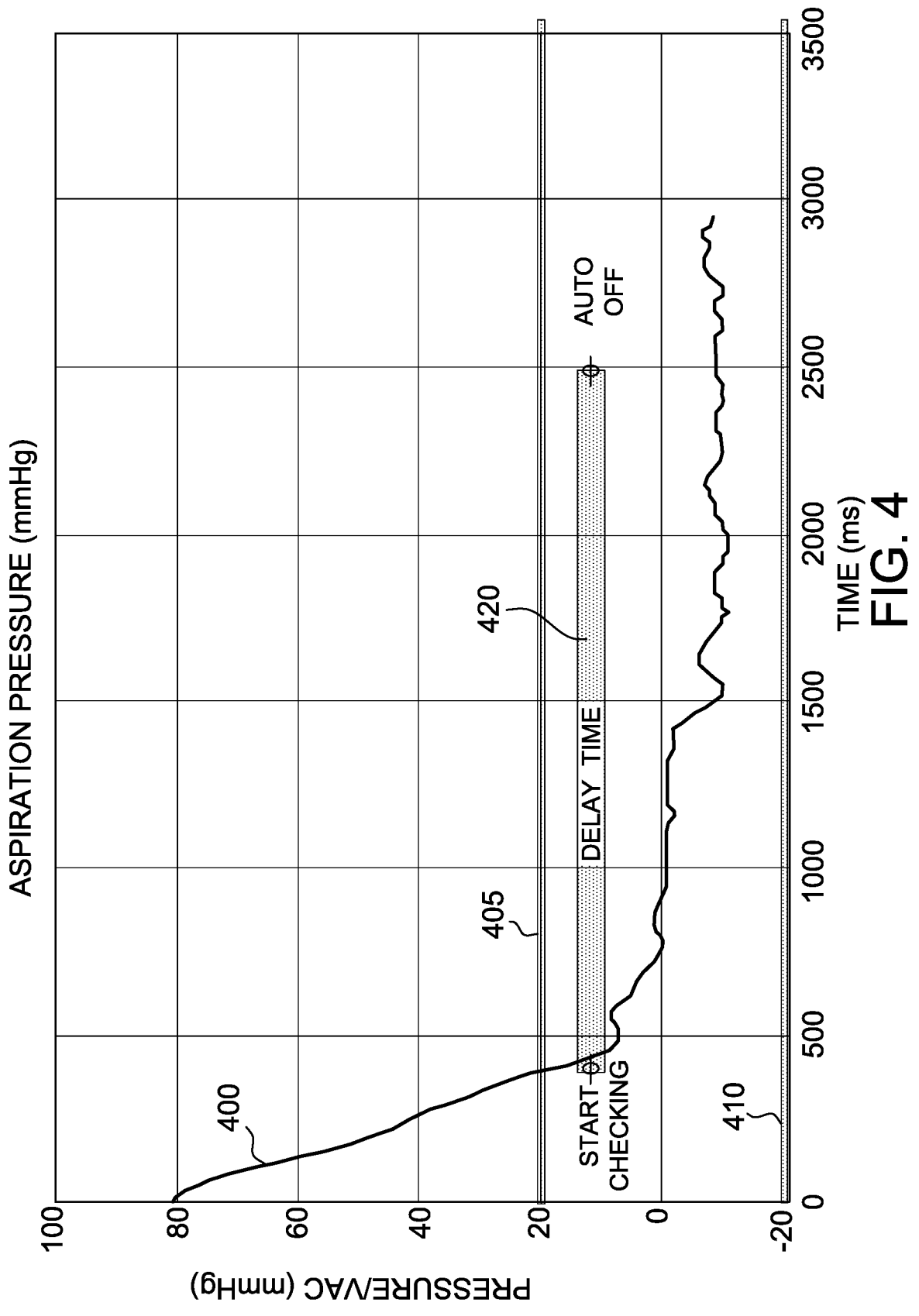
FIG. 4. illustrate system conditions accordance with alternate embodiment of the disclosed invention.

In an alternative embodiment, the algorithm defines a band in which the aspiration vacuum 400 needs to fall in a specified time in order to automatically turn off the continuous irrigation as illustrated in FIG. 4. In this embodiment, the algorithm may provide a user selection for delay time 420 with a band of pressure defined by upper pressure boundary 405 and lower pressure boundary 410. For example, an about 2000 millisecond time delay may be selected and may be programmed to be of any time delay desired by the user of the system. Once following conditions are met, algorithm begins to increment a counter up to the user selected delay time. Once the user selected delay has elapsed, the algorithm may turn the continuous irrigation off.

Figure 5A:
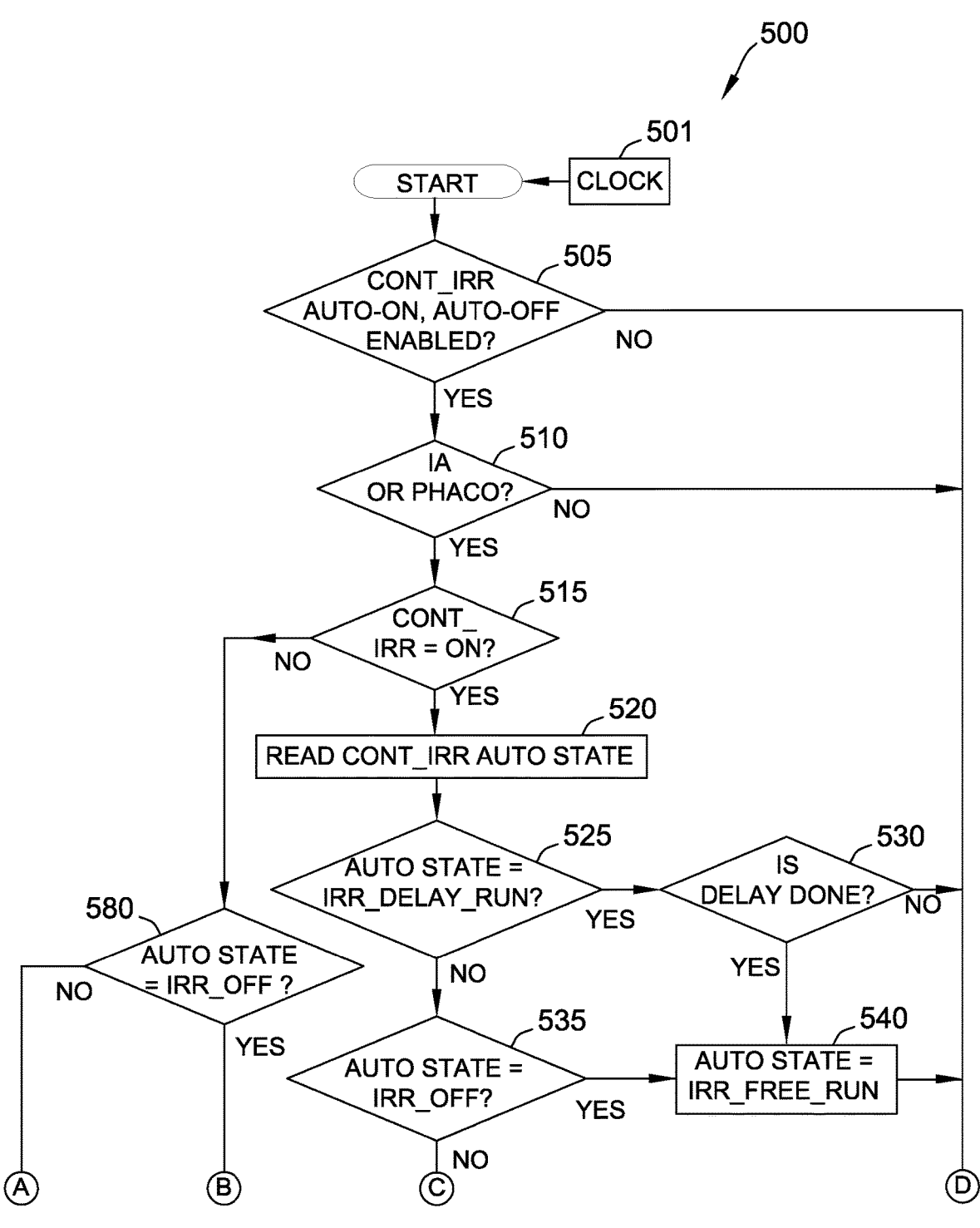
FIGS. 5A and 5B are collectively a flow diagram illustrating an exemplary embodiment of the present invention.
Figure 5B:
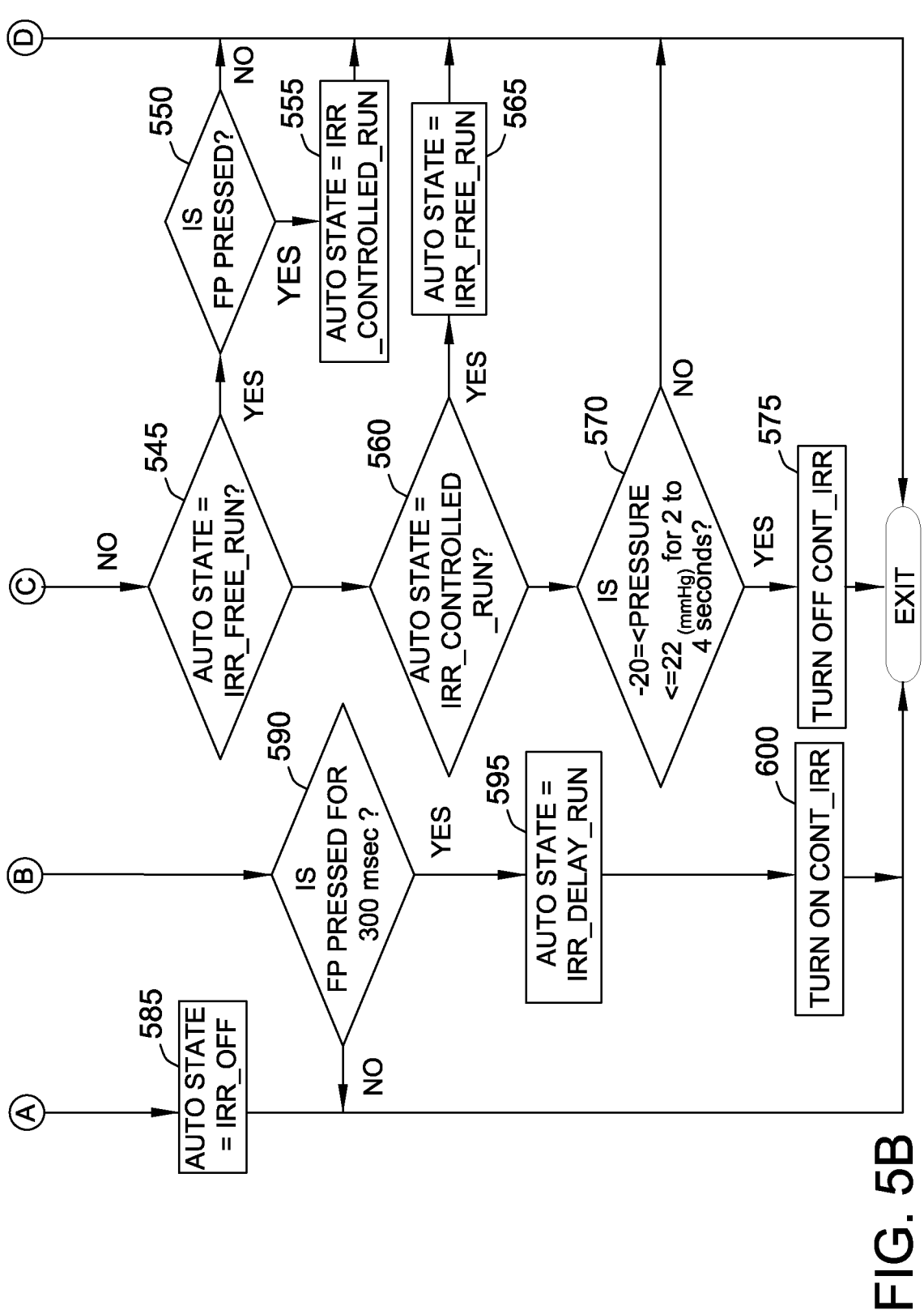

In an embodiment illustrated in FIGS. 5A and 5B, certain conditions may trigger an embodiment of the auto-off process 500 to begin a counter up to the user selected delay time utilizing clock 501 which may be associated with the system of the present invention. As illustrated, in step 505, the continuous irrigation auto-off feature may be enabled with the system checking to see if the system is in Phaco or IA surgical mode in step 510. If either mode is active, continuous irrigation may be turned on through step 515 which may lead into the continuous reading of irrigation state conditions, such as pressure and time, for example, at step 520. The continuous reading of irrigation state conditions may continue through other processes, such as the selected time delay at least partially administered through step 525 and step 530 such that a completed time delay may result in free running irrigation at step 540 and may lead to the exiting and repeating on the steps in FIGS. 5A and 5B. Alternatively, without a time delay and no automatic irrigation in step 535, free running irrigation may continue at step 545. If irrigation is in a controlled state at step 560, the irrigation may be returned to free running irrigation at step 565, otherwise the system will measure the aspiration pressure of the system at step 570 and will either turn off the continuous irrigation at step 575 or may return to the step 505. More specifically, step 570 may, for example, provide for the monitoring of aspiration pressure which may fall within pre-determined bands, such as between −20 mmHg to +20 mmHg, and which may remain in this band for user selected delay. Satisfaction of the step may turn off the continuous irrigation at step 575.

If back at step 515 continuous irrigation is not on, the system may check to see if the automatic irrigation state is not off at step 560. If the automatic irrigation state is not off, it may be turned off at step 585 before returning to the beginning of process 500. If the automatic irrigation state is off, the system may look to confirm whether a foot pedal associated with the system is actuated in a predetermined manner at step 590, which may result in setting the automatic state to an irrigation delay run at step 595 and may, in turn, activate continuous irrigation at step 600. Foot pedal actuation may be include movement between zones, such as the foot pedal has traveled to at least Zone 1 and released to idle (Zone 0) and/or the foot pedal is depressed for a period of time.

Those of skill in the art will appreciate that the herein described apparatuses, engines, devices, systems and methods are susceptible to various modifications and alternative constructions. There is no intention to limit the scope of the invention to the specific constructions described herein. Rather, the herein described systems and methods are intended to cover all modifications, alternative constructions, and equivalents falling within the scope and spirit of the disclosure, any appended claims and any equivalents thereto.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

The invention claimed is:

1. A system for controlling irrigation fluid flow in a phacoemulsification surgical system, the system comprising:

a surgical handpiece comprising a probe, the probe comprising a probe tip for insertion into a surgical site;

an irrigation fluid source connected to an irrigation feed line, wherein the irrigation feed line coupled with the probe tip;

an aspiration line providing at least a partial vacuum for removing material from the surgical site through the probe tip;

at least one pressure sensor in communication with the aspiration line;

at least one valve in communication with the irrigation feed line; and a controller coupled with the irrigation fluid source and the at least one valve, wherein the controller and the irrigation fluid source are configured to provide irrigation fluid flow through the irrigation feed line and the probe tip to the surgical site while the probe tip is inserted into the surgical site and while a continuous irrigation function is enabled, a volume of the irrigation fluid flow balancing a volume of the material removed from the surgical site, wherein the controller is configured to disable the continuous irrigation function when the probe tip is removed from the surgical site, wherein disabling the continuous irrigation function comprises controlling the at least one valve to restrict the irrigation fluid flow through the irrigation feed line for reduced irrigation fluid usage; and wherein the controller is configured to determine the probe tip is removed from the surgical site at least based upon an aspiration pressure differential exceeding a value and based on at least one predetermined system attribute, wherein the aspiration pressure differential is equal to a first measurement of aspiration pressure minus a second measurement of aspiration pressure over a predetermined time.

2. The system of claim 1, wherein the irrigation fluid source provides gravity fed irrigation fluid.

3. The system of claim 1, wherein the irrigation fluid source is in a bottle or bag.

4. The system of claim 1, wherein the irrigation fluid source provides pressurized irrigation fluid.

5. The system of claim 1, wherein the at least one predetermined system attribute is selected from a graphical user interface (GUI).

6. The system of claim 1, wherein the at least one predetermined system attribute is selected from the group consisting of foot pedal position, a minimum aspiration pressure; and a change in operation mode.

7. The system of claim 1, wherein the aspiration pressure differential is equal to about 20 mmHg.

8. The system of claim 1, wherein the aspiration pressure differential is between about 20 mmHg and 40 mmHg.

9. The system of claim 1, wherein the predetermined time is between 0.5 and 2.5 milliseconds.

10. The system of claim 1, wherein the predetermined time is about 2.5 milliseconds.

11. The system of claim 1, wherein the predetermined time is about 1.5 milliseconds.

12. The system of claim 1, wherein the predetermined time is about 1.0 milliseconds.

13. The system of claim 1, wherein the predetermined time is about 0.5 milliseconds.

14. The system of claim 1, wherein the controller is configured to take the first measurement of aspiration pressure on a condition that a measured aspiration pressure has changed by more than about 5% from a previous value.

15. The system of claim 1, wherein the controller is configured to take the first measurement of aspiration pressure on a condition that a measured aspiration pressure has changed by more than 10% from a previous value.

16. A method for controlling irrigation fluid flow in a phacoemulsification surgical system, the method comprising:

measuring a change in aspiration pressure;

providing an irrigation fluid flow through an irrigation feed line and to a surgical site while a probe tip of a probe is inserted into the surgical site and while a continuous irrigation function is enabled, a volume of the irrigation fluid flow balancing a volume of material removed from the surgical site through an aspiration line;

disabling the continuous irrigation function when the probe tip is removed from the surgical site, wherein disabling the continuous irrigation function comprises restricting the irrigation fluid flow through the irrigation feed line by at least one valve for reduced irrigation fluid usage, and determining the probe tip is removed from the surgical site at least based upon a change in aspiration pressure exceeding a value and based on at least one system attribute, wherein the change in aspiration pressure is equal to a first measurement of aspiration pressure minus a second measurement of aspiration pressure over a period of time.

17. The method of claim 16, wherein the at least one system attribute is selected from the group consisting of foot pedal position, a minimum aspiration pressure; and a change in operation mode.

18. The method of claim 16, wherein the change in aspiration pressure is equal to about 20 mmHg.

19. The method of claim 16, wherein the change in aspiration pressure is between about 20 mmHg and 40 mmHg.

20. The method of claim 16, wherein the measuring occurs between 0.5 and 2.5 milliseconds.

21. The method of claim 16, wherein the measuring occurs about every 2.5 milliseconds.

22. The method of claim 16, wherein the measuring occurs about every 1.5 milliseconds.

23. The method of claim 16, wherein the measuring occurs about every 1.0 milliseconds.

24. The method of claim 16, wherein the measuring occurs about every 0.5 milliseconds.

25. The system of claim 1, wherein the controller is configured to take the first measurement of aspiration pressure and the second measurement of aspiration pressure.

26. The system of claim 1, wherein the controller is configured to reenable the continuous irrigation function when the probe tip is reinserted into the surgical site.

27. The method of claim 1, further comprising:

reenabling the continuous irrigation function when the probe tip is reinserted into the surgical site.

* * * * *